(12) United States Patent
Wietelmann et al.

(10) Patent No.: US 6,693,212 B1
(45) Date of Patent: Feb. 17, 2004

(54) TRIS(OXALATO)PHOSPHATES, METHOD FOR THEIR PREPARATION AND THEIR USE

(75) Inventors: Ulrich Wietelmann, Friedrichsdorf (DE); Klaus Schade, Wiesbaden (DE); Uwe Lischka, Niedereschbach (DE)

(73) Assignee: Chematall GmbH, Frankfurt am Main (DE)

( * ) Notice: Subject to any disclaimer, the term of this patent is extended or adjusted under 35 U.S.C. 154(b) by 0 days.

(21) Appl. No.: 10/030,221

(22) PCT Filed: May 12, 2000

(86) PCT No.: PCT/EP00/04301

§ 371 (c)(1),
(2), (4) Date: May 23, 2002

(87) PCT Pub. No.: WO01/07450

PCT Pub. Date: Feb. 1, 2001

(30) Foreign Application Priority Data

Jul. 22, 1999 (DE) .......................... 199 33 898

(51) Int. Cl.$^7$ .............................. C07F 9/06; H01M 4/00
(52) U.S. Cl. ..................... 558/73; 429/231.95
(58) Field of Search ............................. 558/70, 73, 74; 429/122, 231.9, 231.95

(56) References Cited

U.S. PATENT DOCUMENTS

2002/0161247 * 10/2002 Bonrath et al. ............. 549/411

OTHER PUBLICATIONS

CA:85:46129 abs of Tetrahedron Letters by Gloede et al (12) pp 917–20 1976.*
CA:130:156006 abs of Electrocehmical and Solid State Letters by Handa et al 2(2) pp 60–62 1999.*
CA:134:117122 abs of Organic Letters by Lacour et al 2(26) pp 4185–4188 2000.*
CA:129:253905 abs of Chemical Communications ( Cambridge) by Lacour et al (16) pp 1733–1734.*
CA:76:20778 abs of Journal of the Chemical Society section D Chemical Communications by Chang et al (18) pp 1070–1 1971.*

* cited by examiner

*Primary Examiner*—Jean F. Vollano
(74) *Attorney, Agent, or Firm*—Antonelli, Terry, Stout & Kraus, LLP

(57) ABSTRACT

The invention relates to tris-(oxalato)phosphates of the general formula $M[P(C_2O_4)_3]$ wherein M=H, a metal or $N(R^1R^2R^3R^4)$, where $R^1, R^2, R^3, R^4$, are independently H or an alkyl group comprising 1 to 8 C atoms. The invention also relates to a method for preparing such compounds as well as to their use.

20 Claims, 3 Drawing Sheets

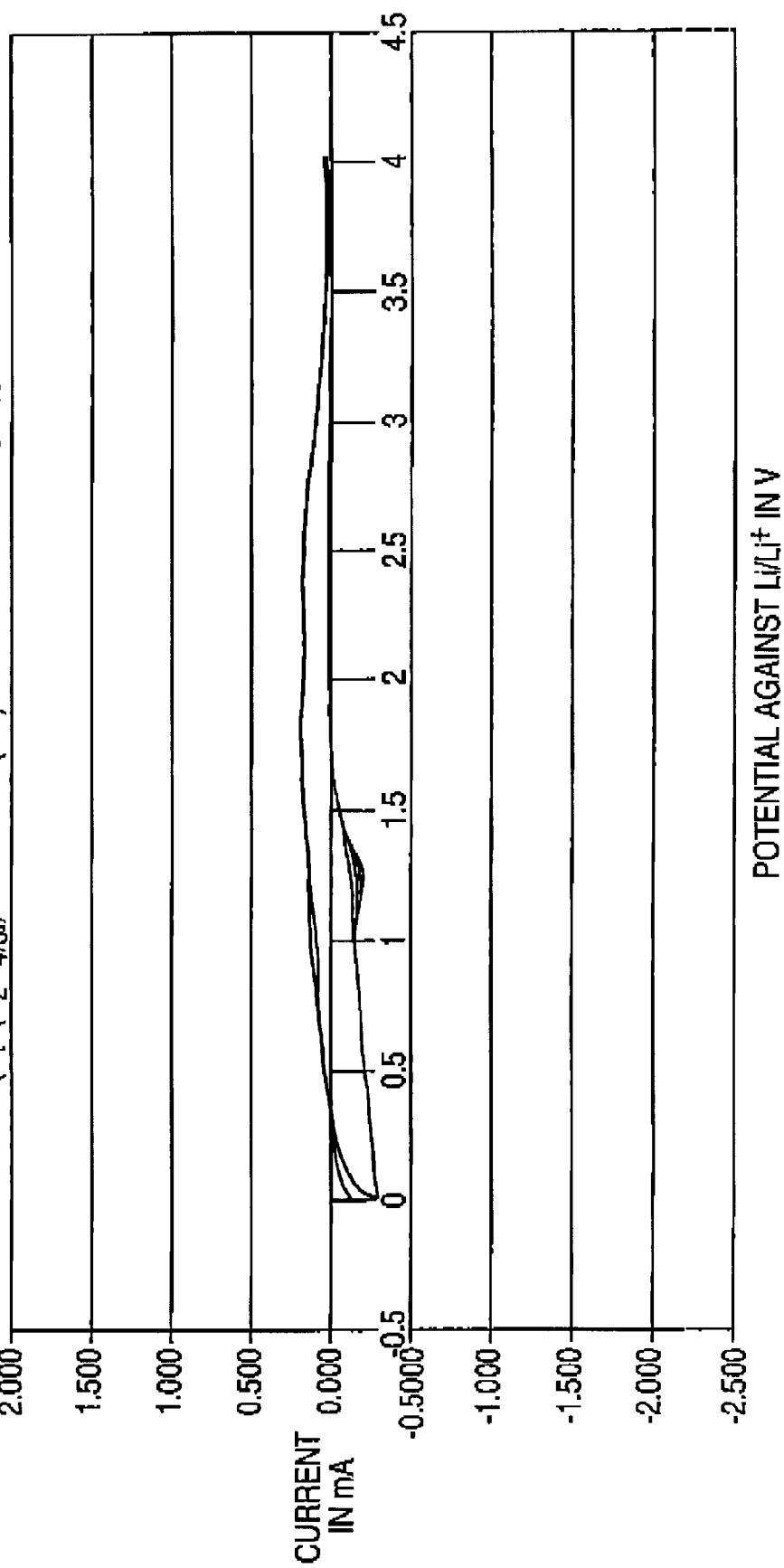

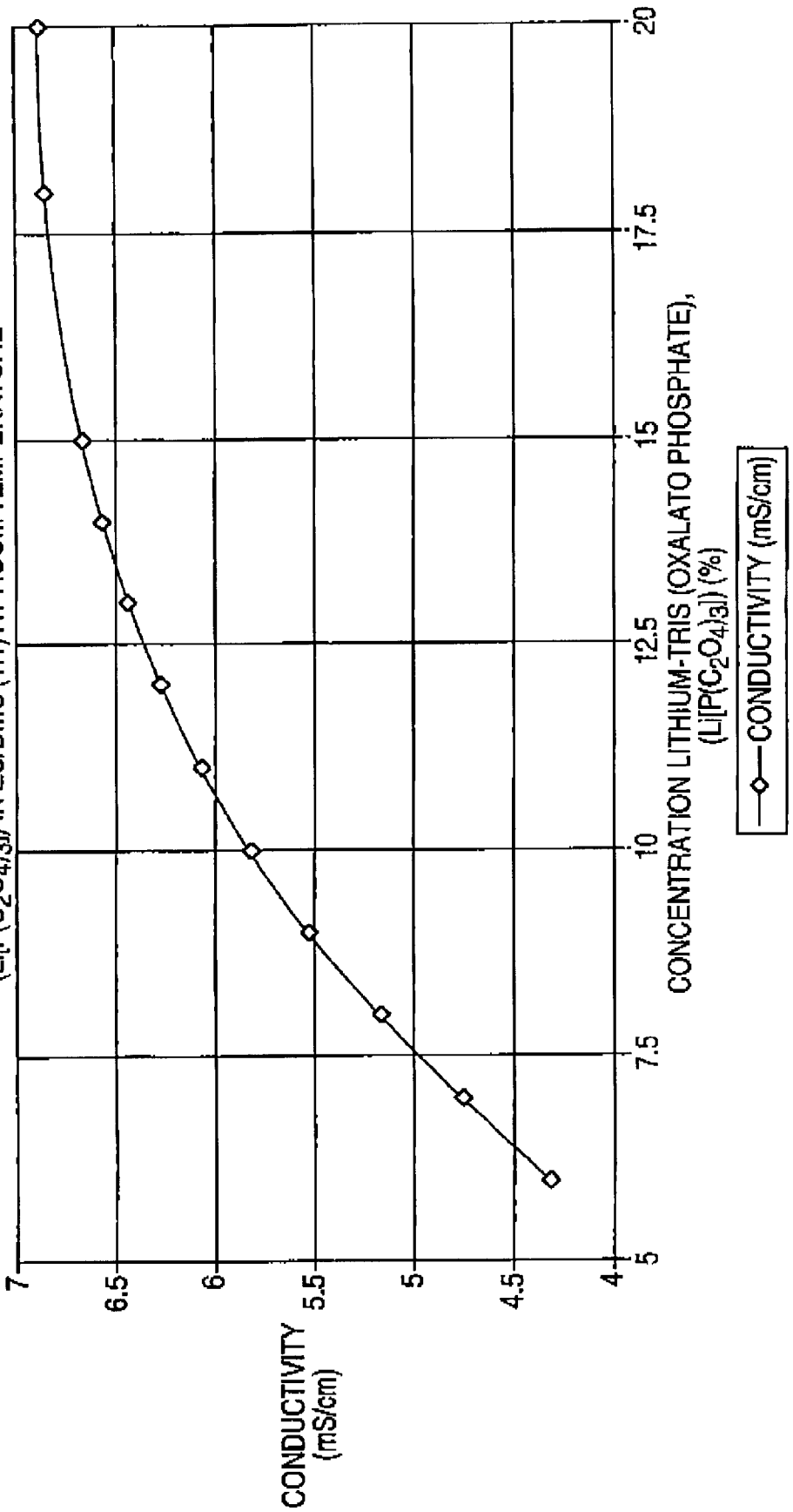

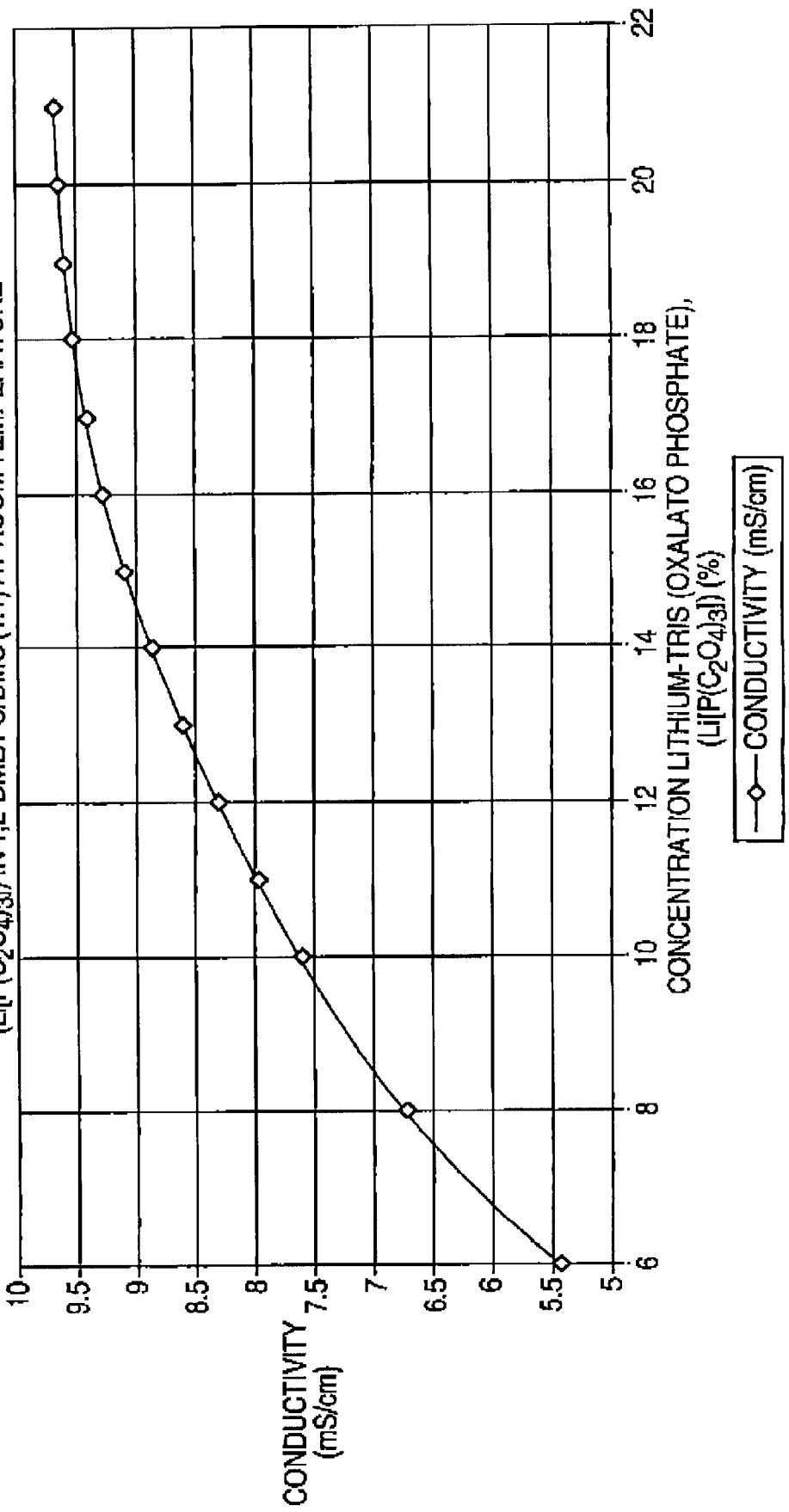

TRIS(OXALATO)PHOSPHATES, METHOD FOR THEIR PREPARATION AND THEIR USE

This application is a 371 of PCT/EP/00/04301 filed May 12, 2000 now WO 01/07450.

The invention relates to tris(oxalato)phosphates, M[P$(C_2O_4)_3$], a method for their preparation and the use of tris(oxalato)phosphates, inter alia, as conducting salts in electrochemical storage systems.

Electrochemical storage systems are e.g. batteries and so-called supercapacitors. Electrolyte solutions comprising a conducting salt and an aprotic solvent are used in these systems. Modern systems, such as e.g. lithium ion batteries, have a high power density and output voltage (often≧3 V). Aprotic electrolyte systems are required for these cells.

Lithium hexafluorophosphate (LiPF$_6$) is currently used as the conducting salt in all commercial lithium ion batteries. This salt has the necessary prerequisites for use in high-energy cells, i.e. it is readily soluble in aprotic solvents, it leads to electrolytes with high conductivities, and it has a high degree of electrochemical stability. Oxidative decomposition occurs only at potentials>approx 4.5 V.

However, LiPF$_6$ also has serious disadvantages which are chiefly attributed to its lack of thermal stability. A dissociation, although slight, into LiF and PF, which can lead to cationic polymerization of the solvent caused by the Lewis acid PF, takes place in solution.

On contact with moisture, corrosive hydrogen fluoride is liberated, which on the one hand makes handling difficult because of its toxicity and corrosiveness, and on the other hand can lead to (partial) dissolution of the transition metal oxides employed as the cathode material (e.g. LiMn$_2$O$_4$). The cycle stability of the electrochemical energy store concerned is affected in this manner.

Against this background, there have been intensive efforts with the aim of developing alternative conductive salts. Above all, lithium salts with perfluorinated organic radicals have been tested as such salts. In particular lithium trifluoromethanesulfonate, lithium bis(trifluoromethanesulfonyl)-imide and the lithium methides, the simplest parent substance of which is lithium tris(trifluoromethanesulfonyl)methide, have been mentioned. These salts also have disadvantages which have so far impeded their use in commercial lithium batteries. The first mentioned salt does not impart a sufficiently high conductivity to the electrolytes prepared with it. The salts mentioned last indeed have a conductivity equivalent to that of LiPF$_6$, but they are of no commercial interest because of the expensive preparation process. Furthermore, the imide is corrosive towards aluminium sheets, which are employed as current diverters in many battery systems. Because of the high fluorine content of the compounds, exothermic reactions with the lithium of the electrode are, moreover, to be feared under adverse conditions.

Lithium hexafluorophosphate and all the abovementioned conductive salt alternatives have the common feature of a rather high fluorine content. On the basis of this fact, the preparation costs are comparatively high and certain safety precautions have to be taken in the disposal or recycling of spent batteries in order to avoid emission of fluorine-containing substances (e.g. toxic and corrosive hydrogen fluoride HF).

The lithium borate complex salts [(R'O)$_2$B(OR")$_2$]Li described in DE 19633027 A1 represent a considerable advance. In these, R' and R" are the same or different, R' and R" are optionally bonded to one another by a single or double bond, and R' and R" in each case individually or together denote an aromatic ring from the group consisting of phenyl, naphthyl, anthracenyl or phenanthrenyl, which can be unsubstituted or mono- to tetrasubstituted by A or Hal, wherein Hal represents fluorine or chlorine and A is an alkyl residue having 1 to 8 C atoms, which can in turn be mono- to tetrahalogenated.

The stabilities of the non-fluorinated derivatives, which are indeed improved, but are in no way adequate for the 3 V systems required, are a disadvantage of these compounds. Thus, e.g. unsubstituted lithium bis[1,2-benzenediolato(2-)-O,O']borate(1-) (which is the 2:1 complex of pyrocatechol) already decomposes when an anodic potential of 3.6 V is exceeded. This value is significantly below that of the standard conductive salt LiPF$_6$ (approx. 4.5 V). Even in the case of these chelatoborates, too, only fluorine-substituted derivatives are sufficiently stable to oxidation.

A chelatophosphate, namely lithium tris[1,2-benzenediolato(2)-O,O']phosphate, has been tested as another alternative (M. Handa, M. Suzuki, J. Suzuki, H. Kanematsu, Y. Sasaki, Electrochemical and Solid-State Letters, 2 (2) 60–62 (1999)). This salt has a wider electrochemical stability range than the corresponding boron compound (start of decomposition from about 3.7 V), but the maximum conductivities which can be achieved for electrolyte solutions prepared with this are below 4 mS/cm; i.e. significantly below the standard given by LiPF$_6$.

Salts with large cations (e.g. N(R$^1$R$^2$R$^3$R$^4$)$^+$, wherein R$^1$, R$^2$, R$^3$ and R$^4$ are independently of one another H or an alkyl group having 1 to 8 C atoms, are commonly used for supercapacitors since these are largely inert towards the electrode materials.

The invention is therefore based on the object of eliminating the disadvantages of the prior art and of providing halogen-free electrochemically stable and thermally stable compounds which are readily soluble in aprotic solvents and are suitable for the preparation of electrolyte solutions with a good conductivity. Furthermore, catalysts should be found, such as those employed, for example, for the hydroamination of amines. The invention is furthermore based on the object of providing a method for the preparation of these compounds.

The object is achieved with tris(oxalato)phosphates of the general formula M[P(C$_2$O$_4$)$_3$], where N=H, a metal or N(R$^1$R$^2$R$^3$R$^4$), wherein R$^1$, R$^2$, R$^3$ and R$^4$ independently of one another are H or an alkyl group having 1 to 8 C atoms. Metal tris (oxalato) phosphates are as preferred compounds and hydrogen tris(oxalato)phosphate, lithium tris (oxalato) phosphate and sodium tris(oxalato)phosphate are as particularly preferred compounds.

It has been found, surprisingly, that these tris(oxalato) phosphates have the required property profiles and furthermore are easy to prepare. The compounds are readily to very readily soluble in polar-aprotic solvents.

BRIEF DESCRIPTION OF THE DRAWINGS

FIG. 1 is a cyclic voltammogram of a solution of lithium-tris(oxalato phosphate), (Li[P(C$_2$O$_4$)$_3$]) in EC/DMC (1:1) against an Ni electrode.

FIG. 2 is a graph showing the conductivity of a solution of lithium-tris(oxalato phosphate), (Li[P(C$_2$O$_4$)$_3$]) in EC/DMC (1:1) at room temperature.

FIG. 3 is a graph showing the conductivity of a solution of lithium-tris(oxalato phosphate), (Li[P(C$_2$O$_4$)$_3$]) in 1,2-DME/PC/DMC (1:1) at room temperature.

Lithium tris(oxalato)phosphate has been investigated in more detail. The solubilities in various polar-aprotic solvents are shown in Table 1.

TABLE 1

Solubilties of lithium tris(oxalato)phosphate

| Solvent | Max. concentration | |
|---|---|---|
| | wt. % | mol/kg |
| THF | 34.5 | 1.1 |
| 1,2-DME | 53 | 1.7 |
| EC/DMC (1:1) | 16 | 0.54 |
| PC/1,2-DME (1:1) | 39.0 | 1.30 |
| Et$_2$O | almost insoluble | |
| Alkanes/aromatics | insoluble | |

THF = tetrahydrofuran; 1,2-DME = 1,2-dimethoxyethane; EC = ethylene carbonate; DMC = dimethyl carbonate; PC = propylene carbonate; Et$_2$O = diethyl ether THF=tetrahydrofuran; 1,2-DME=1,2-dimethoxyethane; EC=ethylene carbonate; DMC=dimethyl carbonate; PC=propylene carbonate; Et$_2$O=diethyl ether According to thermogravimetric findings, decomposition starts only above 150° C. The specific conductivities are significantly above those of the chelatophosphate compound described by Handa et al.: In binary carbonate mixtures up to approx. 7 mS/cm is recorded. If ether-functionalized co-solvents, such as e.g. tetrahydrofuran (THF), ethylene glycol ether, polyethers or 1,3-dioxolane, are added, even significantly higher conductivities are measured. A 20% solution in propylene carbonate/1,2-dimethoxyethane (1:1) thus has a conductivity of 9.7 mS/cm. On inert electrodes (e.g. platinum or nickel), electrochemical decomposition only starts significantly at above 4 V (see FIG. 1).

To prepare tris(oxalato)phosphates, in a first reaction step phosphorus pentachloride is reacted with anhydrous oxalic acid in the presence of an aprotic solvent according to the following equation:

$$PCl_5 + 3C_2O_4H_2 \rightarrow H[P(C_2O_4)_3] + 5HCl$$

For this, the oxalic acid is expediently initially introduced into the solvent and PCl$_5$ is measured in (on a laboratory scale with e.g. a solids measuring bulb). However, it is also possible initially to introduce PCl$_5$ into the solvent and then to add the oxalic acid. An ether (e.g. diethyl ether, tetrahydrofuran, 1,2-dimethoxyethane) or a carbonate (e.g. ethylene carbonate, dimethyl carbonate, diethyl carbonate, propylene carbonate) or a hydrocarbon (e.g. alkane having 5 to 12 C atoms or aromatics, such as e.g. benzene or toluene) or a halogenated hydrocarbon or a partly halogenated hydrocarbon or a mixture of these substances can be employed as the aprotic solvent. Depending on the dissolving power of the solvent used, the two reactants are at least partly dissolved (e.g. with ethers as the solvent) or merely suspended (e.g. with hydrocarbons as the solvent). The reaction temperature is −20 to 120° C., preferably 0 to 100° C. It has been found that the reaction was usually complete within a few minutes to hours (depending on the batch size, rate of addition of the reactants, dissolving power of the solvent, temperature).

The hydrogen chloride (HCl) forming as a by-product already largely escapes during the synthesis via the gas phase, depending on the solvent chosen and the reaction temperature. For use of the later product as a conductive salt in electrochemical systems, it is necessary for this to be largely freed from chloride, e.g. the chloride content in lithium tris(oxalato)phosphate should be<20 ppm.

There are several possibilities for the complete removal of HCl: When the reaction is complete, by boiling the reaction mixture under reflux, stripping by passing an inert gas stream (e.g. nitrogen or argon) through the reaction container, carrying out the reaction under reduced pressure or distilling off some or all of the solvent. When the solvent is removed completely, the chelatophosphoric acid is obtained as a solid, which can be liberated completely from volatile acid impurities under reduced pressure at temperatures of preferably 20 to 50° C.

In some cases, e.g. if diethyl ether is used as the solvent, the hydrogen chloride can also be removed by liquid/liquid separation. This is possible because two liquid phases are formed during the reaction: a heavy phase which contains the desired intermediate product in the form of an ether complex and little HCl, and a light phase floating on top in which the HCl is concentrated. Since the phosphorus compound is only very poorly soluble in ether, no noticeable amounts of product are to be found in the upper phase. The upper phase is separated off and the lower phase containing the intermediate product is extracted several times with pure ether, until no further acid is detectable in the upper phase.

Several of these process steps can also be combined for removal of HCl which is as complete as possible.

The intermediate product tris(oxalato)phosphoric acid (hydrogen tris(oxalato)phosphate), which is, as far as possible halide-free, is converted into the metal tris(oxalato) phosphate in a subsequent reaction step by reaction with the corresponding metal or metal derivative according to the following equations $$H[P(C_2O_4)_3] + M \rightarrow M[P(C_2O_4)_3] + \tfrac{1}{2}H_2, \text{ or}$$

$$H[P(C_2O_4)_3] + M'B \rightarrow M'[P(C_2O_4)_3] + BH$$

in an aprotic solvent, described above, at temperatures of 0 to 80° C., preferably 10 to 50° C. All metals can be employed as the metals M but Li, Na, K, Rb and Cs are preferred. If a polyvalent metal (e.g. Mg, Zn or rare earths) is employed, the stoichiometry in the formulae given is to be adjusted accordingly. A preferred metal derivative M'B comprises a cation of the alkali metals mentioned or an ammonium or a substituted ammonium ion (N(R$^1$R$^2$R$^3$R$^4$)$^+$, wherein R$^1$, R$^2$, R$^3$ and R$^4$ independently of one another are H or an alkyl group having 1 to 8 C atoms, and a base B, wherein B=H or C(R$^{1'}$R$^{2'}$R$^{3'}$) or N(R$^{1'}$R$^{2'}$) or OR'', wherein R$^{1'}$, R$^{2'}$ and R$^{3'}$ independently of one another are H or an alkyl group having 1 to 8 C atoms and R'' is an alkyl group having 1 to 8 C atoms.

Examples of alkali metal derivatives are hydrides (LiH, NaH, KH, RbH, CsH), organometallic compounds (e.g. methyllithium, butyllithium), amides (e.g. LiNH$_2$, NaNH$_2$, KNH$_2$ or lithium diisopropylamide) or alkoxides (e.g. Li tert-butoxide, Na tert-butoxide, Na tert-amoxide, K tert-butoxide). The hydrides and organometallic compounds are particularly preferred, since these are very reactive, easily removable, form acceptable by-products (hydrogen or the organic residues in the form of alkanes) and are commercially available.

To prepare the ammonium salt, dry ammonia NH$_3$ is passed in as the "metal derivative" M'B:

$$H[P(C_2O_4)_3] + NH_3 \rightarrow NH_4[P(C_2O_4)_3]$$

The quaternary ammonium salts can be prepared by double decomposition.

$$M''[P(C_2O_4)_3] + X[N(R^1R^2R^3R^4)] \rightarrow [N(R^1R^2R^3R^4)][P(C_2O_4)_3] + M''X$$

where M"=H, Li, Na, K, Rb, Cs and where X=F, Cl, Br, I, $NO_3$.

The intermediate compound where M"=H is preferred here, since in this case volatile acid, which can be removed via the gas phase, is formed in the reaction. If M"=Li, Na, K, Rb or Cs, a solvent in which M"X is insoluble is to be chosen, e.g. diethyl ether or hydrocarbons.

When the reaction has taken place, the product can remain in solution or can be liberated from the solvent by e.g. evaporation and drying. The product can be recrystallized for further purification.

The metal tris(oxalato)phosphates according to the invention of the general formula $M[P(C_2O_4)_3]$ are used as conductive salts in electrochemical storage systems, and in particular lithium tris(oxalato)phosphate $Li[P(C_2O_4)_3]$ can be used as a conductive salt in lithium ion batteries.

The tris(oxalato)phosphates according to the invention, in particular the free acid hydrogen tris(oxalato)phosphate, find use as catalysts and additives in organic synthesis, e.g. analogously to the compounds and reaction mechanisms described by Tokunaga, Eckert and Wakatsuki ("Ruthenium-catalysed intermolecular hydroamination of terminal alkines with anilines: a practicable synthesis of aromatic ketimines", Angew. Chem. 1999, 111, no. 21, p. 3416–3419). It has been found there e.g. that $HPF_6$ and $HBF_4$ and their particular ammonium salts are effective additives in the hydroamination of alkines.

The subject matter of the invention is explained in more detail with the aid of the following examples:

EXAMPLE 1

Preparation of Lithium Tris(oxalato)phosphate in Diethyl Ether 52.95 g (588 mmol) of oxalic acid (3% excess) were dissolved in 300 ml ether in a 500 ml three-necked flask and 39.59 g (190.2 mmol) of $PCl_5$ were added by means of a measuring bulb in the course of 5 min. During this procedure, the reaction mixture heated up to the reflux temperature.

After the end of the measuring in the mixture was refluxed for two hours, a total of 6.5 l (approx. 270 mmol=approx. 28% of theory) HCl gas escaping.

After cooling to room temperature, the upper phase was decanted off and the lower product phase was washed with 4×200 ml ether. The upper phases were analysed:

|  | Amount (g) | Acid content (mmol/g) | Total amount of acid (mmol) | % of theory |
|---|---|---|---|---|
| 1st decanting | 184.5 | 3.90 | 720 | 76 |
| 1st washing | 142 | 0.73 | 104 | 11 |
| 2nd washing | 133 | 0.11 | 15 | 1.6 |
| 3rd washing | 148 | 0.065 | 10 | 1.1 |
| 4th washing | 136 | 0.061 | 8 | 0.8 |
|  |  |  |  | Σ  90.5 |

$\delta^{31}$P-NMR:

1st decanting: signal group in the range of 0 to 10 ppm, diluted, weak signal at −141.3 ppm
lower phase: −141.4 ppm; integral=1
4th washing: no $^{31}$P-NMR signal The lower phase was evaporated to dryness, in vacuo, at a final bath temperature of 70° C. A finely crystalline white solid remained.

The residue was suspended in about 200 ml diethyl ether, and 7.9 g LiH were added. Since hardly any $H_2$ gas was evolved during stirring for 45 minutes at room temperature, the mixture was refluxed for approx. 5 hours, 2.9 l of gas (ether-saturated hydrogen) escaping. A further 3.9 l of gas were evolved during further stirring for 14 hours at room temperature. The ether was distilled off, the residue was taken up in 300 ml THF, and 0.95 g LiH was added. After stirring for 15 minutes, the mixture was filtered very slowly. Cl⁻ was not detectable in the filtrate.

Li (FES)=0.462 mmol/g
P (ICP)=0.438 mmol/g
Cl⁻ (argentometr.)=<6·10⁻⁶ mmol/g
FES=flame emission spectroscopy
ICP=inductively coupled plasma emission spectroscopy The solution was evaporated and the remaining solid was dried in vacuo at room temperature. The partly coagulated, partly crystalline product was ground in a mortar in a glove box and then dried again in vacuo.

Yield: 48.8 g (=85% of theoretical; losses by sampling are not taken into account)

EXAMPLE 2

Recrystallization of Lithium Tris(oxalato)phosphate in THF 20.34 g lithium tris(oxalato)phosphate were dissolved in 38.5 g THF. A further 22 g THF and 64 g toluene were added and the clear solution was concentrated by distillation. The first distillate passed over at an overhead temperature of 82° C. The overhead temperature rose continuously to 98° C. (amount of distillate 60 g). At this point the solution separated to form two liquid phases. A further 21 g toluene were added and the mixture was cooled with vigorous stirring. Two liquid phases were still to be observed at room temperature. The lower crystallized at ice-bath temperature. It was filtered and the colourless solid residue was dried in vacuo.

Yield: 21.1 g lithium tris(oxalato)phosphate still containing residual moisture.

$\delta^{31}$P: −141.3 ppm, no impurities.

EXAMPLE 3

Preparation of Trisoxalatophosphoric Acid (Hydrogen Tris(oxalato)phosphate)

158.9 g (1.764 mol) of dried oxalic acid were initially introduced into 490 g (700 mol) of diethyl ether in a 1 l four-necked flask with an intensive cooler, thermocouple, KPG stirrer and heating mushroom and 118.8 g (0.572 mol) $PCl_5$ were added via a metering bulb in the course of 20 min. The oxalic acid solution heated up to the boiling point (36° C.) with relatively vigorous evolution of gas. After the end of the measuring, the mixture was refluxed for 140 minutes. After a few minutes the reaction solution separated to form two clear phases. After the stated time 17.0 l (approx. 0.688 mol, approx. 24% of theory) HCl gas (measured with a paraffin-filled gas meter) had developed.

After cooling to room temperature, the upper phase was separated off via an immersed tube and the lower product-containing phase was washed with 587 g $Et_2O$ divided into 5 portions. The last ether phase still contained 0.069 mmol H⁺/g. The oil (lower phase) obtained was characterized by spectroscopy after addition of a little $C_6D_6$:

$\delta^1$H: 1.08 (t) intensity 57; 3.70 (q) intensity: 38; 14.11 (s) intensity: 4.5

$\delta^{13}C$: 14.4; 68.8; 153.4 (d)

$\delta^{31}P$: −141.6

It is thus a trisoxalatophosphoric acid-ether adduct of approximate composition $H[P(C_2O_4)_3.]4Et_2O$.

Approx. 20 ml of the oily trisoxalatophosphoric acid-ether adduct prepared in this way were dried in vacuo for 10 minutes at room temperature. After a short time the oil solidified to a colourless solid. The weight was determined (17.7 g) and the solid was dried to constant weight for a further 3 hours at room temperature and then for 2 hours at 45 to 50° C.

Yield: 14.1 g of ether-free, finely crystalline trisoxalato-phosphoric acid.

(The weight loss corresponds to the removal of one mol of ether per mol of trisoxalatophosphoric acid.)

P=2.7 mmol/g

NMR data from a solution in dimethyl carbonate:

$\delta^{31}P$=−141.6 ppm $\delta^1H$=12.4 ppm, additional signals from the solvent $\delta^{13}C$=153.7 ppm, additional signals from the solvent TGA:=670% weight loss at $T_{max}$=108° C.

Melting point: 112° C.; (TGA thermogravimetric analysis).

EXAMPLE 4

Preparation of a Lithium Tris(oxalato)phosphate Electrolyte Solution 300 ml $Et_2O$ were added to 315 g of the oily trisoxalato-phosphoric acid-ether adduct (contains approx. 0.53 mol trisoxalatophosphoric acid) from Example 3, and 4.8 g LiH (0.606 mol, 114% of theory) were added in the course of 30 minutes. Vigorous evolution of gas occurred during this procedure and the internal temperature rose almost to the boiling point. After a short time a white salt precipitated out. After stirring for a total of one hour at 30 to 35° C., 14.25 l of gas (ether-saturated hydrogen) had formed. A further 0.48 g of LiH was added, after which a further 520 ml of gas escaped within 1 hour.

The suspension was filtered over a G3 glass filter (5 minutes) and the residue on the filter was rinsed with 168 g $Et_2O$ in 2 portions. The filter-moist, only very slightly dried cake weighed 205.1 g; it was dried to constant weight for 3 hours first at room temperature and then further at 60° C.

Yield: 130.2 g of finely powdered lithium tris(oxalato) phosphate (=0.431 mmol=810 of theory); Cl: not detectable; P: 3.25 mmol/g; Li: 4.8 mmol/g (still contains excess LiH); $\delta^{13}C$: 53.6 ppm, solution in $THF/C_6D_6$; $\delta^{31}P$: −141.7 ppm, solution in $THF/C_6D_6$; TGA: start of decomposition>160° C., $T_{max}$=183° C.,; Weight loss to 600° C.=74%.

The electrolyte solution was then prepared as follows: 80.5 g of lithium tris(oxalato)phosphate were dissolved in 427 g of EC/DMC (1:1 mixture) (scarcely perceptible heat effect; somewhat insoluble, partly flocculent residue) and the mixture was first degassed and vented with argon. After heating up to 70° C., a total of 10.8 g LiH were added in several portions by means of a metering bulb. The evolution of gas over a period of approx. 10 hours in total was 1,390 ml=58 mmol. The suspension was cooled and filtered over a thoroughly heated glass filter.

Yield: 450 g; Conductivity: 7.05 mS/cm at 20° C.; $\delta^{31}P$: −141.4 ppm; Li: 0.50 mmol/g (=15.1% lithium tris(oxalato) phosphate).

EXAMPLE 5

Neutralization of Trisoxalatophosphoric Acid With Butyllithium

A trisoxalatophosphoric acid-ether adduct was prepared analogously to Example 3. The lower oily phase (approx. 76 g, 130 mmol) was diluted with approx. 100 ml of $Et_2O$ and cooled to 0° C., and 130 mmol of a 1.6 molar butyllithium solution in hexane were added. The reaction was highly exothermic (ice bath) and a colourless salt precipitated out. After heating to room temperature, the mixture was filtered and the residue was washed with 3×50 ml ether and dried in vacuo.

Yield: 33.5 g lithium tris(oxalato)phosphate (85% of theoretical).

EXAMPLE 6

Preparation of Sodium Tris(oxalato)phosphate Solution

A trisoxalatophosphoric acid-ether adduct was prepared analogously to Example 3. The lower oily phase (approx. 93 g, 155 mmol of acid) was dissolved in 150 ml of THF at 0° C., and approx. 180 mmol of NaH powder (measuring bulb, several portions) were added. After the evolution of $H_2$ had subsided, the mixture was warmed to room temperature and stirred for 3 hours. The cloudy solution was filtered.

Yield: 165 g of colourless solution $\delta^{31}P$: −141.0 ppm; Na=0.86 mmol/g=142 mmol (=92% of theoretical).

What is claimed is:

1. A tris(oxalato)phosphate selected from the group consisting of compounds of the general formula, $M[P(C_2O_4)_3]$ where M=H, a Li, Na, K, Rb, Cs or $N(R^1R^2R^3R^4)$ and, wherein $R^1$, $R^2$, $R^3$ and $R^4$ independently of one another are H or an alkyl group having 1 to 8 C atoms and compounds of the general formula $M[P(C_2O_4)_3]_2$ wherein M=Zn or Mg and wherein $R^1$, $R^2$, $R^3$ and $R^4$ independently of one another are H or an alkyl group having 1 to 8 C atoms.

2. Hydrogen tris(oxalato)phosphate, $H[P(C_2O_4)_3]$.

3. Lithium tris(oxalato)phosphate, $Li[P(C_2O_4)_3]$.

4. Sodium tris(oxalato)phosphate, $Na[P(C_2O_4)_3]$.

5. Method for the preparation of hydrogen-tris(oxalato) phosphate, $H[P(C_2O_4)_3]$, characterized in that phosphorus pentachloride is reacted with anhydrous oxalic acid in the presence of an aprotic solvent and the HCl gas formed is removed.

6. Method for the preparation of a tris(oxalato)phosphate of the general formula $M[P(C_2O_4)_3]_x$, where M=a metal selected from the group consisting of Li, Na, K, Rb, Cs, Zn and Mg, or $N(R^1R^2R^3R^4)$ wherein $R^1$, $R^2$, $R^3$ and $R^4$ independently of one another are H or an alkyl group having 1 to 8 C atoms, and wherein, when M is $N(R^1R^2R^3R^4)$, Li, Na, K, Rb or Cs, x is 1 and when M is Zn or Mg, x is 2, characterized in that in a first reaction step, phosphorus pentachloride is reacted with anhydrous oxalic acid in the presence of an aprotic solvent to form hydrogen-tris(oxalato)phosphate as an intermediate product and wherein HCl gas is formed, which is removed, and, in a second reaction step, the intermediate product formed is reacted with the corresponding metal M as defined above or a metal derivative wherein the metal derivative is a compound consisting of a cation of a metal M as defined above and a base or a compound consisting of $N(R^1R^2R^3R^4)^+$, wherein $R^1$, $R^2$, $R^3$ and $R^4$ are as defined above, and a base, in the presence of an aprotic solvent to give the tris(oxalato)phosphate of the general formula $M[P(C_2O_4)_3]_x$, and wherein the tris(oxalato) phosphate formed either remains in solution or is isolated as a solid.

7. Method according to claim 5, characterized in that, in the method, an ether or a carbonate or a hydrocarbon or a halogenated hydrocarbon or a mixture of these substances is employed as the aprotic solvent.

8. Method according to claim 5, characterized in that the method is carried out at a temperature of −20 to 120° C.

9. Method according to claim 8, characterized in that the method is carried out at a temperature of 0 to 100° C.

10. Method according to claim 5, characterized in that the HCl gas formed in the method is removed by boiling the reaction mixture under reflux or by stripping by means of an inert gas stream or by reducing the pressure or by distilling off some or all of the solvent or by a liquid/liquid separation or by a combination of these process steps.

11. Method according to claim 6, characterized in that, in the second reaction step, an ether or a carbonate or a hydrocarbon or a halogenated hydrocarbon or a mixture of these substances is employed as the aprotic solvent.

12. Method according to claim 6, characterized in that the second reaction step is carried out at a temperature of 0 to 80° C.

13. Method according to claim 12 characterized in that the second reaction step is carried out at a temperature of 10 to 50° C.

14. Method according to claim 6 for the preparation of lithium tris(oxalato)phosphate, $Li[P(C_2O_4)_3]$.

15. Method according to claim 6 for the preparation of sodium-tris(oxalato)phosphate, $Na[P(C_2O_4)_3]$.

16. Method according to claim 6, characterized in that the first reaction step is carried out at a temperature of −20 to 120° C.

17. Method according to claim 16, characterized in that the first reaction step is carried out at a temperature of 0 to 100° C.

18. Method according to claim 6, characterized in that the HCl gas formed in the first reaction step is removed by boiling the reaction mixture under reflux or by stripping by means of an inert gas stream or by reducing the pressure or by distilling off some or all of the solvent or by a liquid/liquid separation or by a combination of these process steps.

19. A conducting salt in an electrochemical storage systems wherein the conducting salt comprises a tris(oxalato)phosphate of the general formula $M[P(C_2O_4)_3]$, where M is Li, Na, K, Rb or Cs, or wherein the conducting salt comprises a tris(oxalato)phosphate of the general formula $M[P(C_2O_4)_3]_2$ where M is Zn or Mg.

20. A conducting salt in a lithium ion battery wherein the conducting salt comprises lithium tris(oxalato)phosphate of the formula $Li[P(C_2O_4)_3]$.

* * * * *